United States Patent [19]

Cardis et al.

[11] Patent Number: 5,120,457

[45] Date of Patent: Jun. 9, 1992

[54] BENZENESULFONYL DERIVATIVES OF N,N-DIORGANODITHOCARBAMIC ACIDS AS MULTIFUNCTIONAL ADDITIVES FOR LUBRICATING OIL COMPOSITIONS

[75] Inventors: Angeline B. Cardis, Florence; Abraham O. M. Okorodudu, West Deptford, both of N.J.

[73] Assignee: Mobil Oil Corp., Fairfax, Va.

[21] Appl. No.: 579,527

[22] Filed: Sep. 10, 1990

[51] Int. Cl.$^5$ .................................... C10M 135/10
[52] U.S. Cl. ................... 252/47.5; 562/879; 564/75
[58] Field of Search ............ 252/47.5; 562/879; 564/75

[56] References Cited

U.S. PATENT DOCUMENTS

| | | | |
|---|---|---|---|
| 3,682,980 | 8/1972 | Braid et al. | 260/396 |
| 3,810,890 | 5/1974 | Dunbar et al. | 564/75 |
| 3,900,471 | 8/1975 | Dunbar et al. | 564/75 |
| 3,919,212 | 11/1975 | Dunbar et al. | 564/75 |
| 4,758,362 | 7/1988 | Butke | 252/47.5 |
| 4,859,356 | 8/1989 | Okorodudu | 252/47.5 |
| 4,919,830 | 4/1990 | Farng et al. | 252/327 |

OTHER PUBLICATIONS

CA 102 (23): 203614a.
CA 111 (1): 7166c.
CA 86 (3): 16610k.

*Primary Examiner*—Prince Willis, Jr.
*Assistant Examiner*—Jerry D. Johnson
*Attorney, Agent, or Firm*—Alexander J. McKillop; Charles J. Speciale; Howard M. Flournoy

[57] ABSTRACT

Products derived from the reaction of organic or metal salts of diorganodithiocarbamic acids with benzenesulfonyl halides, impart excellent multifunctional antiwear and antioxidant properties to lubricating oil compositions.

11 Claims, No Drawings

BENZENESULFONYL DERIVATIVES OF N,N-DIORGANODITHOCARBAMIC ACIDS AS MULTIFUNCTIONAL ADDITIVES FOR LUBRICATING OIL COMPOSITIONS

BACKGROUND OF THE INVENTION

1. Field of the Invention

This application is directed to multifunctional antiwear/antioxidant additives for lubricants and to improved lubricant compositions containing same. The additive products of this invention are derived from the reaction of organic or metal salts of diorganodithiocarbamic acids with hydrocarbylbenzenesulfonyl derivatives.

Ashless dithiocarbamates are a valuable class of compounds as potential replacements for their metal structural analogs in the lubricant industry and in a market in which the prevailing and projected tendency favors non-metallic additives. The products of this invention have demonstrated excellent antioxidant and antiwear effectiveness in lubricating oil compositions and have the potential advantage over the metal analogs, of better solubility in, and compatibility with, a variety of base stocks. Another advantage of these sulfonyl derivatives is the potential reserve alkalinity needed to neutralize acidic by-products while in service.

It has now been discovered that the products obtained from the reactions of dithiocarbamic acid salts and benzene sulfonyl derivatives, lubricating compositions containing same, and use of such compositions provide the unexpected & highly desirable benefits itemized below.

2. Description of Related Art

A variety of dithiocarbamate-derived compounds are known to be useful in lubricant compositions. For example, U.S. Pat. No. 4,919,830 is directed to dihydrooarbyl dithiocarbamate-derived organic phosphates which have been found to be effective multifunctional additives for various lubricant media and U.S. Pat. No. 4,859,356 is directed to reaction products derived from amine or metal salts of N,N-diorganodithiocarbamic acids with alkylthiiosulfinyl halides useful as multifunctional additives in lubricating oil compositions.

More specifically it has been found that products derived from the reaction of the organic or metal salts of N, N-diorganodithiocarbamic acids with alkylbenzenesulfonyl halides impart excellent multifunctional antiwear and antioxidant protection t lubricating oil compositions.

SUMMARY OF THE INVENTION

This application discloses and is more particularly directed to the reaction products of organic or metal salts of N,N-diorganodithiocarbamic acids with hydrocarbylbenzenesulfonyl derivatives which when added to lubricants, provide multifunctional antioxidant and antiwear properties thereto. This application is also directed to improved antioxidant/antiwear lubricant compositions and to a method of using these novel additive reaction products.

It is, therefore, an object of this invention to provide improved lubricant compositions, novel multifunctional lubricant additives, and the use of the herein described novel additive products of reaction in such compositions.

DESCRIPTION OF THE PREFERRED EMBODIMENTS

The tertiary amine, e.g. triethylammonium salts of N, N-diorganodithiocarbamic acids are readily prepared by reacting equimolar quantities of triethylamine, a secondary amine, and carbon disulfide in an organic solvent such as toluene or hexane, according to Equation 1. Similarly, the metal, e.g., sodium salts are prepared by using sodium hydroxide instead of the tertiary amine, as shown in Equation 2.

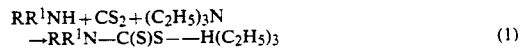
(1)

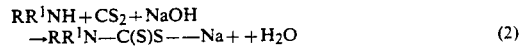
(2)

The products of this invention may then be prepared by reacting these salts with, for example, an alkylbenzenesulfonyl halide as shown in Equation 3. Other sulfonyl halides include but are not limited to toluene sulfonyl chloride, dodecylbenzenesulfonyl chloride and p,t-butyl benzenesulfonyl chloride or other benzenesulfonyl halides or alkylbenzensulfonyl halides or the like or mixtures thereof.

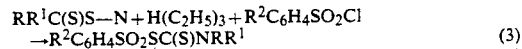
(3)

where R and $R^1$ are the same or different and R and $R^1$ are each a hydrocarbyl group containing from 1 to about 36 carbon atoms or $C_1$-$C_{36}$ hydrocarbyls having at least one heteroatom which can be oxygen, sulfur or nitrogen and where hydrocarbyl is selected from alkyl, alkenyl, aryl, aralkyl, alkaryl groups and can contain phenyl, naphthyl, anthryl substituents; R and $R^1$ can be a $(CH_n)m$ group comprising part of an alicyclic or heterocyclic system selected from, for example, pyrrole, pyrrolidine, piperidine, morpholine etc, where n is 1 or 2 and m is 2 to 8. $R^2$ is a hydrocarbyl group containing from 1 to 36 carbon atoms and having none or at least one heteroatom which can be oxygen, sulfur or nitrogen, and where hydrocarbyl is selected from alkyl, alkenyl, aryl, aralkyl, alkaryl groups which can contain phenyl, naphthyl or antharyl substituents.

Suitable tertiary amines include but are not limited to the following: trialkyl amines such as triethylamine and tributylamine and tertiary amines such as pyridine, hexamethylene tetramine, 1,4-Diazabicyclo [2,2,2]octane, collidine, and the like. Suitable secondary amines are selected from bis(2-ethylhexyl)amine, dibutylmine, dipropylamine, dicocoamine, didoceylamine and the like. The reaction can be run with other secondary amines, within the following general classes; dialkyl amines, diarylamines, alicyclic amines, heterocyclic amines, etc., or mixtures of such secondary amines, in aprotic solvents such as hexane, toluene, xylenes etc.

A preferred dithiocarbamate salt is the triethylammonium salt of N,N-diorgano dithiocarbamic acid.

Conditions for the above reactions may vary widely depending upon specific reactants, the presence or absence of a solvent and the like. Any suitable set of reaction conditions known to the art may be used. Hydrocarbon solvents, as mentioned hereinabove, such as toluene or xylenes are frequently used. Generally stoichiometric or equimolar ratios of reactants are used. However, more than molar or less than molar amounts may be used. In any event, reaction conditions are not viewed as critical.

The additives embodied herein are utilized in lubricating oil or grease compositions in an amount which imparts significant antioxidant and antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %.

The additives have the ability to improve the antiwear and antioxidant characteristics of various oleagenous materials such as hydrocarbyl lubricating media which may comprise liquid oils in the form of either a mineral oil or a synthetic oil, or a mixture of mineral and synthetic oils, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. The oils having viscosity indexes ranging to about 95 ar preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps including lithium hydroxystearate, for example, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether phenoxy phenylethers.

It is to be understood, however, that the compositions contemplated herein can also contain other materials. For example, corrosion inhibitors, extreme pressure agents additional detergents, dispersants, antiwear agents, co-antioxidants and the like can be used as exemplified respectively by metallic phenates, sulfonates, polymeric succinimides, non-metallic or metallic phosphorodithioates and the like. These materials do not detract from the value of the compositions of this invention, rather the materials serve to impart their customary properties to the particular compositions in which they are incorporated.

The following examples are merely illustrative and not meant to be limitations.

EXAMPLE 1

Bis(2-ethylhexyl)amine, (121 g, 0.5 moles), triethylamine, (60 g, 0.6 moles) and toluene, (150 ml) were charged into a 1-liter reaction flask. To the well-stirred mixture at ambient temperature, carbon disulfide, (45 g, 0.6 moles) was added slowly, dropwise, keeping the exothermic reaction temperature below 35° C. To the triethylammonium salt of the N, N-di-(2-ethylhexyl) dithiocarbamic acid thus formed was added, at ambient temperature, 200 ml of toluene followed by toluenesulfonyl chloride (95 g, 0.5 moles) in portions, at a rate to maintain the exothermic reaction temperature between 50° and 55° C. After the addition, the reaction mixture was heated at about 60° C. for about 3 ½ hrs. It was then filtered at ambient temperature, washed three times with 100 ml portions of water, dried over anhydrous magnesium sulfate, and stripped of solvent to give the product.

Following the procedure of Example 1, but varying the secondary amine and/or the alkylbenzenesulfonyl chloride used, the products of the following examples were prepared.

EXAMPLE 2

The product of this example was obtained from dibutylamine as the secondary amine and p-toluenesulfonyl chloride.

EXAMPLE 3

Dibutylamine and p-t-butylbenzenesulfonyl chloride were used as the secondary amine and the alkylbenzenesulfonyl halide respectively in the preparation of this product.

EXAMPLE 4

The product of this example was obtained by using bis(2-ethylhexyl)amine and dodecylbenzenesulfonyl chloride as the secondary amine and alkylbenzenesulfonyl halide, respectively.

EVALUATION OF PRODUCTS

The additives were blended (1%) into a solvent refined paraffinic neutral base stocks and tested for effectiveness by the B-10 Catalytic Oxidation Test, an antioxidants and in the standard Four-Ball Wear Test machine for antiwear activity. The conditions of the tests, results and comparison of the above sample and other structural analogs with the base oils are shown in Tables 1 and 2.

CATALYTIC OXIDATION TEST

Basically, in the catalytic oxidation test, the lubricant is subjected to a stream of air which is bubbled through at the rate of five liters per hour at elevated temperatures for a specified time (Table 1, 325° F. for 40 hours). Present in the composition are samples of metals commonly used in engine construction, namely, iron, copper, aluminum, and lead.

See U.S. Pat. No. 3,682,980, incorporated herein by reference.

TABLE 1

B-10 CATALYTIC OXIDATION TEST
325° F. 40 HRS

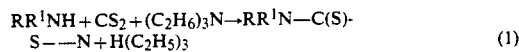

| ITEM | ADDITIVE (1%) | ACIDITY INCR NN | VIS INC % KV | Pb LOSS mg |
|---|---|---|---|---|
|  | None | 17.59 | 142.8 | 5.8 |
| 1 | $R,R^1 = C_8H_{17}$; $R^2 = CH_3$ | 0.1 | 14.4 | 1.1 |
| 2 | $R,R^1 = C_4H_9$; $R^2 = CH_3$ | 1.95 | 15.2 | 1.1 |
| 3 | $RR,R^1 = C_4H_9$; $R^2 = C(CH_3)_3$ | 0.95 | 27.0 | 0.4 |
| 4 | $R,R^1 = C_8H_{17}$; $R^2 = C_{12}H_{25}$ | 2.1 | 35.1 | 0.0 |

The remarkable antioxidant performance of these reaction products is evident, as demonstrated in Table 1 by excellent control of increased in both acidity and viscosity.

In the Four-Ball Wear Test, three stationary balls are placed in the lubricant cup and the lubricant containing the compound to be tested is added thereto, and a fourth ball is placed in a chuck mounted on a device which can be used to spin the ball at known speeds and loads. The samples were tested using ½ inch stainless steel balls of 52100 steel for 30 minutes.

TABLE 2

4-BALL WEAR TEST
½" BALLS, 52100 STEEL,
2000 RPM, 60 KG, 200° F., 30 MIN

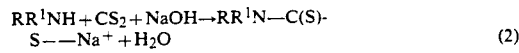

| ITEM | ADDITIVE | WEAR SCAR DIAM (mm) |
|---|---|---|
|  | None | 3.30 |
| 1 | $R,R^1 = C_8H_{17}$; $R^2 = CH_3$ | 0.79 |
| 2 | $R,R^1 = C_4H_9$; $R^2 = CH_3$ | 0.88 |
| 3 | $R,R^1 = C_4H_9$; $R^2 = C(CH_3)_3$ | 0.90 |
| 4 | $R,R^1 = C_8H_{17}$; $R^2 = C_{12}H_{25}$ | 1.51 |

The results of the Four-Ball Wear Tests clearly show the good antiwear activity of these reaction products.

The use of additive concentrations of reaction produces of the above disclosed compositions in premium quality industrial, automotive and marine lubricants will provide improved multifunctional antioxidant/antiwear/anticorrosion properties to such compositions.

Clearly the use of the reaction products of these organic or metal salts of N,N,-diorganodithiocarbamic acids with alkylbenzenesulfonyl halides provides exceptional antiwear and antioxidant activity. The test data show that these ashless, non-phosphorus additives are very effective as multifunctional antiwear, antioxidant additives at low concentrations in lubricant compositions. In addition, the unique structures of these novel compounds make them potential detergent additives while in service.

What is claimed is:

1. An improved lubricant composition comprising a major amount of an oil of lubricating viscosity or grease prepared therefrom and a minor multifunctional antiwear/antioxidant amount of from about 0.001 to about 10 wt % based on the total weight of the composition of a product of reaction prepared by reacting amine or metal salts of N,N-diorganodithiocarbamic acids derived from equimolar amounts of secondary hydrocarbyl amines, tertiary hydrocarbyl amines and carbon disulfide or equimolar amounts of secondary hdyrocarbyl amines, alkali or alkaline earth metal hydroxides and carbon disulfide with hydrocarbylbenzenesulfonyl halides wherein the reaction temperature varies from about ambient to about 100° C., and the molar ratio of said dithiocarbamic acid salt to said sulfonyl halide varies from molar to less than molar to more than molar.

2. The composition of claim 1 wherein the metal is selected from sodium, potassium or calcium.

3. The composition of claim 1 wherein said carbamic acid salt is an amine salt.

4. The composition of claim 1 wherein the product of reaction is prepared by reacting equimolar amounts of said tertiary amine or a metal hydroxide, and secondary amine and carbon disulfide in an inert solvent in the following manner:

$$RR^1NH + CS_2 + (C_2H_6)_3N \rightarrow RR^1N\text{—}C(S)\text{—}S\text{——}N^+H(C_2H_5)_3 \quad (1)$$

$$RR^1NH + CS_2 + NaOH \rightarrow RR^1N\text{—}C(S)\text{—}S\text{——}Na^+ + H_2O \quad (2)$$

where R and $R^1$ are the same or different and R and $R^1$ are each a hydrocarbyl group containing from 1 to 36 carbon atoms or $C_1$-$C_{36}$ hydrocarbyl having at least one heteroatom selected from oxygen, sulfur or nitrogen or R and $R^1$ is a $(CH_n)m$ group comprising part of an alicyclic or heterocyclic system selected from pyrrole, pyrrolidine, piperidine, morpholine where n is 1 or 2 and m is 2 to 8 and where hydrocarbyl is selected from alkyl, alkenyl, aryl, aralkyl and alkaryl groups; and thereafter reacting the product of (1) or (2) with a hydrocarbylbenzenesulfonyl halide in the following manner:

$$RR'N\text{—}C(S)S\text{——}N^+H(C_2H_5)_3 + R^2C_6H_5SO_2Cl \rightarrow R^2C_6H_5So\ SC(S)NRR' \quad (3)$$

or

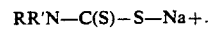

5. The composition of claim 4 wherein the tertiary amine is selected from the group consisting of triethylamine, pyridine, collidine and 1-4-dazabicyclo octane.

6. The composition of claim 5 wherein the tertiary amine is triethylamine.

7. The composition of claim 4 wherein the secondary amine is selected from the group consisting of dialkyl amines, diarylamines, alicyclic amines, heterocyclic amines or mixtures thereof.

8. The composition of claim 7 wherein the secondary amine is selected from the group consisting of bis(2-ethylehexyl)amine, dibutylamine, didodecylamine, dicocoamine, and dipropylamine.

9. The composition of claim 4 wherein the sulfonyl halide is selected from the group consisting of toluenesulfonyl chloride, dodecylbenzenesulfonyl chloride and p-t-butylbenzenesulfonyl chloride.

10. The composition of claim 4 wherein the reactants in accordance with equation (1) in addition to carbon disulfide are bis-(2-ethylhexyl)amine and triethylamine, the product thereof is thereafter reacted with toluenesulfonyl chloride or dodecylbenzenesulfonyl chloride or p-t-butylbenzenesulfonyl chloride.

11. The composition of claim 1 wherein said lubricant is selected from the group consisting of (1) mineral oils, (2) synthetic oils, (3) a mixture of mineral and synthetic oils or (4) is a grease prepared from any one of (1), (2) and (3).

* * * * *

UNITED STATES PATENT AND TRADEMARK OFFICE
CERTIFICATE OF CORRECTION

PATENT NO. : 5,120,457
DATED : June 9, 1992
INVENTOR(S) : Angeline B. Cardis et al.

It is certified that error appears in the above-identified patent and that said Letters Patent is hereby corrected as shown below:

Col. 6, line 53, insert --wherein $R^2$ is a hydrocarbyl group containing from 1 to 36 carbon atoms or $C_1$-$C_{36}$ hydrocarbyl having at least one heteroatom selected from oxygen, sulfur and nitrogen.--

Signed and Sealed this

Twelfth Day of October, 1993

Attest:

BRUCE LEHMAN

*Attesting Officer*  *Commissioner of Patents and Trademarks*